United States Patent
Figueredo et al.

(10) Patent No.: US 11,567,093 B2
(45) Date of Patent: Jan. 31, 2023

(54) BIOLOGICAL SAMPLE READER FOR BIOCHEMICAL TESTING

(71) Applicant: HI TECHNOLOGIES S.A., Curitiba (BR)

(72) Inventors: Marcus Vinicius Mazega Figueredo, Curitiba (BR); Sérgio Renato Rogal Junior, Curitiba (BR); Marcelo Júnior Cossetin, Curitiba (BR); Raquel Dos Santos Verissimo, Curitiba (BR); Renan Nepomoceno Pinto, Curitiba (BR); Alisson Ravaglio Santos, Curitiba (BR); Gabriel Herman Bernardim Andrade, Curitiba (BR); Marcelo Emanuel Melani Camati, Curitiba (BR)

(73) Assignee: HI TECHNOLOGIES S.A., Curitiba (BR)

( * ) Notice: Subject to any disclaimer, the term of this patent is extended or adjusted under 35 U.S.C. 154(b) by 596 days.

(21) Appl. No.: 16/607,809

(22) PCT Filed: Apr. 13, 2018

(86) PCT No.: PCT/BR2018/050100
§ 371 (c)(1),
(2) Date: Oct. 24, 2019

(87) PCT Pub. No.: WO2018/195616
PCT Pub. Date: Nov. 1, 2018

(65) Prior Publication Data
US 2020/0057084 A1    Feb. 20, 2020

(30) Foreign Application Priority Data
Apr. 24, 2017    (BR) .................. 1020170084280

(51) Int. Cl.
*G01N 35/00* (2006.01)
*G01N 21/25* (2006.01)
(Continued)

(52) U.S. Cl.
CPC ....... *G01N 35/00722* (2013.01); *G01N 21/25* (2013.01); *G01N 33/487* (2013.01);
(Continued)

(58) Field of Classification Search
CPC ............. G01N 35/00722; G01N 21/25; G01N 33/487; G01N 35/04; G01N 2035/00019;
(Continued)

(56) References Cited

U.S. PATENT DOCUMENTS

| | | | |
|---|---|---|---|
| 3,633,922 A | 1/1972 | Yokota | |
| 5,307,263 A | 4/1994 | Brown | |

(Continued)

FOREIGN PATENT DOCUMENTS

| | | |
|---|---|---|
| CN | 104969068 | 10/2015 |
| DE | 102013101888 | 8/2014 |
| EP | 3028242 | 6/2016 |

OTHER PUBLICATIONS

"Accu-Chek Aviva meter," Roche Diabetes Care, Inc., date unknown, 4 pages [retrieved online from: www.accu-chek.com/meters/aviva-meter].

(Continued)

*Primary Examiner* — Benjamin R Whatley
*Assistant Examiner* — Curtis A Thompson
(74) *Attorney, Agent, or Firm* — Sheridan Ross P.C.

(57) ABSTRACT

The present patent of invention relates to a reader device for biological samples used in the field of remote laboratory tests (TLR), for clinical diagnostic purposes, based on an optimized design constituted by a cowling (C) with inlet port (OE) and with switch (I); by a holding support (SS) con- (Continued)

Figure 1:
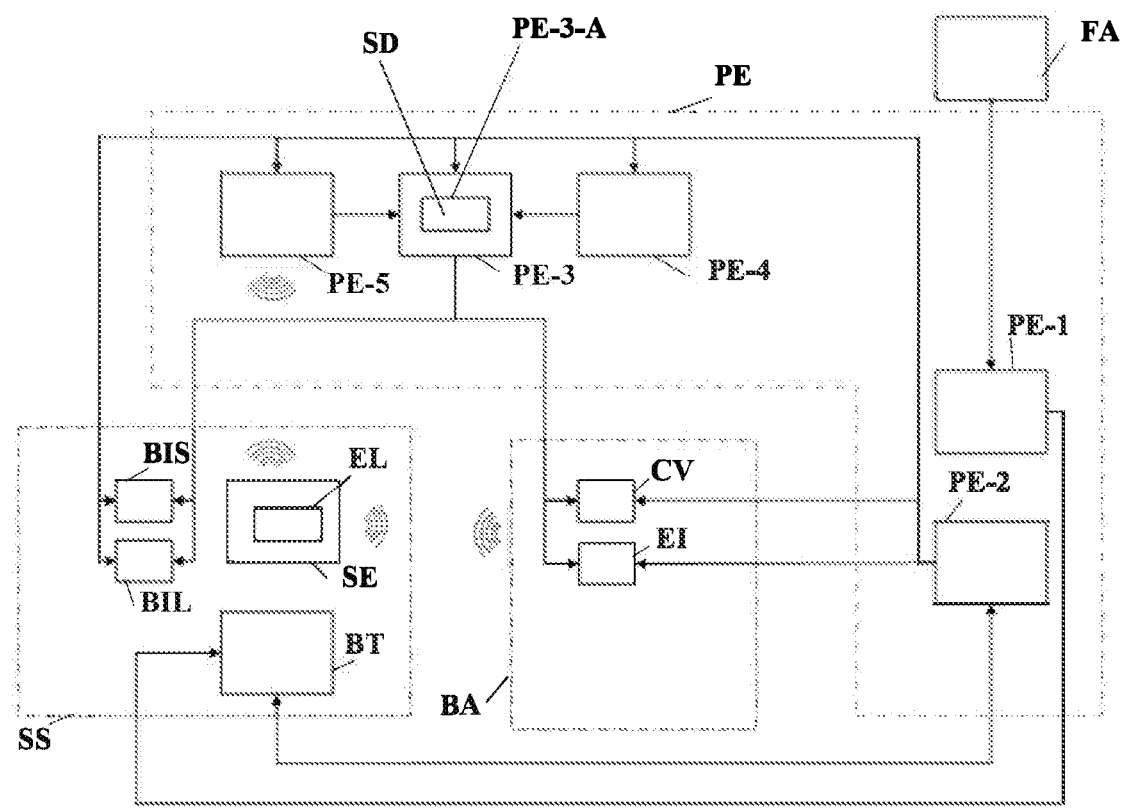

taining a mirror (ES), two batteries (BT), two reading illumination arrays (BIL), operational status illumination arrays (BIS) and an elevator support (SE); by an elevator (EL); by an electronics board (PE) with energy loading circuit (PE-1), with supply circuit (PE-2), with processor (PE-3), with Bluetooth® device (PE-4) and with position sensor (PE-5); and by a base (BA) with software that reads various types of biological samples, the present invention providing the advantages of: ease of use, optimized operating flows, ease of training, modularity, compactness, reduced size, portability, lightness of weight, ergonomic design, used-friendliness, enhanced practically and low cost.

4 Claims, 10 Drawing Sheets

(51) Int. Cl.
*G01N 33/487* (2006.01)
*G01N 35/04* (2006.01)
*G11B 15/675* (2006.01)

(52) U.S. Cl.
CPC ............ *G01N 35/04* (2013.01); *G11B 15/675* (2013.01); *G01N 2035/00019* (2013.01); *G01N 2035/00831* (2013.01); *G01N 2035/00841* (2013.01); *G01N 2035/00851* (2013.01); *G01N 2035/0477* (2013.01)

(58) Field of Classification Search
CPC .......... G01N 2035/00831; G01N 2035/00841; G01N 2035/00851; G01N 2035/0477; G01N 2201/0221; G01N 21/255; G11B 15/675

See application file for complete search history.

(56) References Cited

U.S. PATENT DOCUMENTS

| | | | |
|---|---|---|---|
| 5,899,855 A | 5/1999 | Brown | |
| 6,168,563 B1 | 1/2001 | Brown | |
| 6,295,506 B1 | 9/2001 | Heinonen et al. | |
| 6,471,131 B2 | 10/2002 | Okada et al. | |
| 6,494,830 B1 | 12/2002 | Wessel | |
| 9,311,520 B2 | 4/2016 | Burg et al. | |
| 2003/0234299 A1 | 12/2003 | Hosoda et al. | |
| 2009/0253213 A1* | 10/2009 | Kaneblei | G01N 30/95 422/400 |
| 2013/0189794 A1 | 7/2013 | Emeric et al. | |
| 2014/0154792 A1* | 6/2014 | Moynihan | G01N 33/5302 422/69 |
| 2016/0025639 A1 | 1/2016 | Jakubowicz | |
| 2016/0054316 A1* | 2/2016 | Egan | G01N 21/8483 435/5 |
| 2016/0188937 A1* | 6/2016 | Tyrrell | G01N 35/00029 382/128 |
| 2016/0356801 A1* | 12/2016 | Glavina | G01N 35/0092 |
| 2017/0241999 A1* | 8/2017 | Juez | B01F 31/22 |
| 2019/0317115 A1* | 10/2019 | MacLean | G01N 35/00722 |
| 2020/0300697 A1* | 9/2020 | Cunningham | G01J 3/18 |

OTHER PUBLICATIONS

"Accutrend Plus System," Hoffmann-La Roche Ltd, date unknown, 1 page [retrieved online from: https://diagnostics.roche.com/global/en/products/instruments/accutrend-plus.html].

"Alere Afinion™ AS100 Analyzer Immediate Results Mean Immediate Advice." Abbott, date unknown, 13 pages [retrieved online from: www.alere.com/en/home/product-details/afinion-as100-analyzer-us.html].

"Cholestech LDX™ Analyzer Confidence in Results," Abbott, date unknown, 18 pages [retrieved online from: www.alere.com/en/home/product-details/cholestech-ldx-system.html].

"CoaguChek XS system," Hoffmann-La Roche Ltd, date unknown, 1 page [retrieved online from: diagnostics.roche.com/global/en/products/instruments/coaguchek-xs.html].

"cobas h 232 POC system," F. Hoffmann-La Roche Ltd, date unknown, 8 pages [retrieved online from: diagnostics.roche.com/global/en/products/instruments/cobas-h-232.html].

"PIMA™ Analyser," Abbott, date unknown, 6 pages [retrieved online from: www.alere.com/en/home/product-details/PimaAnalyserOUS.html].

"Reflotron® Plus Information Booklet," BioStat Diagnostic Healthcare, Apr. 2007, 28 pages [retrieved online from: photos.labwrench.com/equipmentManuals/11023-6349.pdf].

"Urisys 1100® analyzer," F. Hoffmann-La Roche Ltd, date unknown, 5 pages [retrieved online from: diagnostics.roche.com/global/en/products/instruments/urisys-1100.html].

International Search Report prepared by the Instituto Nacional da Propriedade Industrial on Jun. 14, 2018, for International Application No. PCT/BR2018/050101.

Official Action for U.S. Appl. No. 16/607,819, dated Mar. 23, 2021 9 pages.

Notice of Allowance for U.S. Appl. No. 16/607,819, dated Jul. 8, 2021 10 pages.

International Search Report prepared by the Institute Nacional da Propriedade Industrial on Jun. 8, 2018, for International Application No. PCT/BR2018/050100.

* cited by examiner

BIOLOGICAL SAMPLE READER FOR BIOCHEMICAL TESTING

CROSS REFERENCE TO RELATED APPLICATIONS

This application is a national stage application under 35 U.S.C. 371 and claims the benefit of PCT Application No. PCT/BR2018/050100 having an international filing date of 13 Apr. 2018, which designated the United States, which PCT application claimed the benefit of Brazil Patent Application No. BR1020170084280 filed 24 Apr. 2017, the disclosures of each of which are incorporated herein by reference in their entireties.

The present patent refers to a reader of biological samples in fast biochemical tests applied in healthcare in general and in Point-Of-Care Testing (POCT) in particular, for the purpose of clinical diagnosis with reduction of the time of release of results and allowing low volume of cartridge-collected biological sample and aiming to provide a quick response that can lead to confirmation or follow-up of a disease through optimized design with mechanics, electronics and dedicated software that reads various types of biological samples, like urine, blood, saliva, mucus, feces and others, bringing advantages of ease of use and optimization of operational flows, easy user training, easy and convenient new test registration, being modular, compact, small in size, portable, lightweight, ergonomic, humanized, intuitive, more practical and cost effective.

As is well known by the technical means linked to the manufacture and use of Point-of-Care Testing (POCT) devices, which analyze reagent cartridges for the detection of infectious, viral, chronic, metabolic disorders, among other biological variables, the following reader devices currently exist:

1. Scanadu Vitals, a device capable of reading vital signs such as oximetry, temperature, pressure and pulse. Scanadu Urine, capable of performing a complete urinalysis test using only a "pee stick" and the application of a camera smartphone. Features: Bluetooth® connectivity for smartphone connection; Uses smartphone for storage, processing and display information obtained from performed exams; Reading of vital signs such as temperature, oximetry, respiratory rate, pulse, blood pressure and stress levels; Sensors for Peripheral Oxygen Saturation (SPO2), infrared thermometer and Electrocardiogram (ECG); Application software (app) with exams history, trends and guide for performing of exams; User registration. Twelve reagents including glucose, leukocytes, nitrite, blood in urine, bilirubin, urobilinogen, microalbumin, creatinine, ketone, specific gravity and its pH levels; and Smartphone application that reads the "pee stick", stores and displays the information.

2. Cube Header Diagnostic System, a test reading system capable of assessing and quantifying lateral flow immunochromatographic assays results based on change of color or appearance of bands. Features: Contains only one button for operation; Has 14 segment LCD display for viewing results; Battery power; Storage capacity of 100 results; and measurement time within approximately 3 seconds.

3. Accu-Chek is a device for measuring and controlling blood glucose levels. Features: Ability to read strips reactive to blood glucose level; Memory capable of storing up to 1000 daily records; Programmable reminders for events, alarm clock and date; Power source: three alkaline or lithium batteries; Color display; Automatic activation that activates and deactivates the device when an exam strip is inserted; The device also turns itself off after downtime; Connectivity: Infrared (IR) data input compatible with proprietary software; Bluetooth® for insulin pump connection; Customizable parameters: Language selection, beep and vibration, bolus calculator, display backlight setting, time format selection, carbohydrate unit selection.

4. Cobas H 232 is a Point-of-Care system for detecting cardiac troponin T, CK-MB, myoglobin and NT-proBNP levels, the levels of these blood substances indicate whether the patient has had an acute myocardial infarction or other cardiac problems recently. Characteristics: Readability of cardiac T troponin, CK-MB, myoglobin, D-dimer and NT-proBNP reagent strips; Memory capable of storing up to 500 test records; Power: AC Power supply; Sample Type: Heparinized whole venous blood; Automatic shutdown programmable between 1 and 60 minutes; and measurement position: Operate the meter on a level and vibration-free surface when applying the sample until the required amount has been fully absorbed by the strip.

5. Urisys 1100 is an urine test strip analyzer. Features: Urine Test Strip Analyzer; Wavelengths: 565 nm and 610 nm; Transfer Rate: 100/h; Memory: 100 results; Interface: 2 line, 24 character LCD screen; Built-in thermal printer; Supported Tests: Density, pH, Leukocytes, Nitrite, Protein, Glucose, Urobilinogen, Bilirubin, Hemoglobin. System Interfaces: Serial computer interface, 5-pin DIN socket for keyboard and barcode reader.

6. Coaguchek XS is intended to measure blood clotting time. Features: TP/INR test strip analyzer; TP time amperometric detection system after activation of coagulation with recombinant human thromboplastin; Handling should be done on level surface and without vibration, keeping the monitor in horizontal position; Memory: 100 test results; Interface: Infrared; Power: Four batteries; Number of tests per battery pack: Up to 300 tests or 2 years in standby; Heparin Sensitivity: No, up to 0.8 I.U/ml for UFH and 2 antiXa for LMWH; Integrated QC: In each strip, through the same channel through which the blood passes.

7. Refroton Plus is an in vitro diagnostic apparatus designed for the quantitative determination of clinical chemistry parameters using reactive strips. It works with reflectance photometry to ensure reliable results. Characteristics: Samples: Blood, plasma and serum; Results in three minutes; Automatic calibration; Fast monitoring; Cardiac risk calculation; Dry chemistry; Method: Photometry and reflectance; performs 17 parameters: Amylase, Pancreatic Amylase, Bilirubin, Cholesterol, CK, Creatine, Alkaline Phosphatase, Gamma GT, Glucose, TGO, TGP, HDL, Hemoglobin, Potassium, Triglyceride, Urea and Uric Acid.

8. Accutrend Plus is a test strip reader capable of performing glucose, cholesterol, triglyceride and lactate tests. Features: glucose, cholesterol, triglyceride and lactate strips analyzer; Measurement ranges: Glucose 20-600 mg/dl (1.1-33.3 mmol/l), cholesterol 150-300 mg/dl (3.88-7.76 mmol/l), triglycerides 70-600 mg/dl (0.80-6.86 mmol/l)), lactate 0.8-21.7 mmol/l (whole blood)—0.7-26 mmol/l (plasma); Sample material a drop of capillary blood; Memory: 100 results; Test principle: Reflectance photometry; and Power: 4 batteries.

9. LABMAXURO120 from Medmax; Features: Test Speed: 120 strips/hour; Memory: 2000 results; Ability to analyze strips of glucose, bilirubin, ketone bodies, density, pH, blood, protein, urobilinogen, nitrite, leukocytes and vitamins C; LCD display; and Interface: RS232 serial port.

10. Afinion AS100 Analyzer is a multi-assay, fast, cartridge analyzer and can be used with various sample types. This device uses Alere Afinion Tests cartridges, which feature exam information code and sample capillary collection system. Features: Performs HbA1c, Lipid Panel, ACR and CRP tests; Color LCD display; USB connection for code reading and exam printing; connectivity compatible with POCT1-A QC and operator lockout.

11. Alere Cholestech LDX System is an analysis device that allows performing of cholesterol, glucose, lipid, and liver enzyme tests. Features: Allows exams for cholesterol, glucose, lipids and liver enzymes; and Simple three-step tests.

12. Alere Prima Analyzer is an assay device for the purpose of counting T cells in a patient's blood. This count helps in the diagnosis and monitoring of patients suffering from immunosuppression caused by the HIV virus. Features: Guarantees the counting result in just 20 minutes; Power: batteries or AC power source; Data file incorporated into the software; Cartridges contain built-in control; Resources: Possibility of immediate implementation of clinical decisions; possibility of operation at the treatment site or in the laboratory; and exam data management (storing, retrieving, printing, reviewing and exporting) and no need for external control of materials.

The products described above are limited to specific types of tests, such as glucose, cholesterol, lipids, among others.

Searching the Brazilian and foreign patent database, we found the following disclosures:

German patent DE102013101888 "Device for optical analysis of test strip with substance for detection of analyte", which discloses a device with a receiving unit for receiving a test strip, and a light source, for example LED, for excitation of a substance from the test strip. A detector or CCD array is arranged to detect the light emitted by the substance from the test strip, where the substance emits or reflects light when the substance comes into interaction with an analyte. A mirror or deflection unit is arranged to reflect light emitted from the test strip to the detector. The deflection unit is arranged in such a way that only light emitted by the test strip substance falls into detector. An independent claim also includes a method for optical analysis of a test strip with a substance for detecting an analyte.

U.S. Pat. No. 6,295,506 "Measurement Apparatus" which discloses a system for measuring the blood glucose level in a sample of a patient's blood. Consumable test strips are provided together with a code which identifies the manufacturing batch of the strip. A measurement unit is provided and is coupled to a mobile telephone. The measurement unit is arranged to receive a test strip and to determine a color change in a reagent due to reaction of the reagent with a blood sample. The identification code is read at the same time by the measurement unit and is transmitted by the mobile telephone to a central database provided by the test strip manufacturer. The database contains identification codes together with associated calibration data. Upon receipt of an identification code, the remote database transmits the associated calibration data to the mobile telephone which uses the calibration data to calculate a test result from the measured change in color. The result can be displayed to the patient on a display of the telephone.

U.S. Pat. No. 9,311,520, which discloses methods and electronic devices for performing color-based reaction testing of biological materials. The method includes capturing and interpreting digital images of an unexposed and later exposed paddle at various delay times within an automatically calibrated environment. The test paddle includes a unique identification mechanism (UID), a Reference Color Bar (RCB) providing samples of standardized colors for image color calibration, compensation and corrections, and several test-specific sequences of Chemical Test Pads (CTP). The method further includes locating the paddle in the image, extracting the UID and validating the paddle, extracting the RCB and locating the plurality of CTP in each image. The method further reduces image noise in the CTP and calibrates the image automatically according to lighting measurements performed on the RCB. To determine test results, the method further determines several distances between the CTP and its possible trajectory in the color space described by the Interpretation Color Chart.

Chinese patent CN104969068, which discloses Methods and electronic devices for performing color-based reaction testing of biological materials. The method includes capturing and interpreting digital images of an unexposed and later exposed paddle at various delay times within an automatically calibrated environment. The test paddle includes a unique identification mechanism (UID), a Reference Color Bar (RCB) providing samples of standardized colors for image color calibration, compensation and corrections, and several test-specific sequences of Chemical Test Pads (CTP). The method further includes locating the paddle in the image, extracting the UID and validating the paddle, extracting the RCB and locating the plurality of CTP in each image. The method further reduces image noise in the CTP and calibrates the image automatically according to lighting measurements performed on the RCB. To determine test results, the method further determines several distances between the CTP and its possible trajectory in the color space described by the Manufacturer Interpretation Color Chart (MICC). The method shows these results in graphical or quantified mode.

Readers disclosed in U.S. Pat. No. 9,311,520 and CN104969068 require a cartridge color template to compensate for differences in illumination. This increases the complexity of construction and operation. Also, as the cartridge is a user-manipulated part, the jig is subject to malfunction.

DE102013101888 does not mention features for recognizing the exam to be performed and so does U.S. Pat. No. 6,295,506B1 for glucose testing.

Readers revealed in the inventions found in searches do not provide resources to send/share exam results to another device.

"BIOLOGICAL SAMPLE READER FOR FAST BIOCHEMICAL TESTING", object of the present patent, has been developed to overcome the drawbacks, limitations and disadvantages of current readers by means of a special mechanical device that houses and positions the cartridge with the sample in the correct position inside the reader and provided with electronics with sensor and processor with dedicated software that reads various types of biological samples like urine, blood, saliva, mucus, feces and others with any kind of examination that produces results based on color variation, bringing advantages of ease of use and operational flow optimization, easy user training, easy and convenient new exam registration, being modular, compact, small in size, portable, lightweight, ergonomic, humanized, intuitive, more practical and cost effective.

The reader of the present invention uses a camera to take measurements and automatically identify the exam to be taken. Using the camera also facilitates future changes, such as changes in cartridge shape and adding of new information (for example, lot, expiration, and country of manufacture) to the cartridge body to be provided to the reader. As soon as the biological sample is deposited in the cartridge, it is inserted into a reader platform that is only released upon completion of the exam. This ensures greater precision in timing of chemical reactions that occur on the test strips, thus making the results more reliable. The reader of the present invention also has a battery to ensure that electrical failures do not invalidate the examination. Using the battery allows the equipment to be used even in places without mains power.

The reader of the present invention does not require lighting compensation as the cartridge lift platform is sealed and ensures a controlled environment, that is, the lighting is always constant regardless of the environment.

Additionally, the reader from the present invention has the following characteristics:

1. External look: Compact, lightweight, ergonomic, humanized and intuitive to traditional equipment. The light lines make it intuitive to use modularly, by changing the cover it is possible to operate with cartridges of different shapes;

2. Automatic identification of exam type: The user does not need to state what type of exam will be taken. This feature also eliminates human error in reporting an incorrect exam;

3. Automatic Cartridge Correction: The cartridge reader and cover design allows the cartridges to remain in the same position for reading at all times. It does not require the user to adjust the position;

4. General Product: Compact, portable and inexpensive. Battery usage makes the product portable and mobile as it eliminates the need for the product to always be plugged into a power outlet. More practical than traditional methods due to automation of parameter identification, positioning and definition. These features also allow the registry of new exams easily and conveniently.

5. Mirror Reflection: Allows equipment size reduction;

6. Cartridge reading module is controlled by local remote hardware: allows cost savings as one device can control multiple readers.

7. In the present invention, once the exam is completed, the result may be transmitted to another device with compatible communication. This feature allows for integrating the reader with other systems, making it easy to implement functions such as processing, printing, storage and management. Also, it is possible a low-cost version of readers where no screen is used and a device can receive and display results from one or several readers.

Currently existing readers have the following technical problems that the present invention solved:

1. Cartridge entry error in the reader, solved by the present invention by the special shape of the cartridge and the reader having an upper entry where the cartridge can only be inserted if it is in the correct snap position. This avoids operating errors;

2. The positioning of the cartridge in the reader is not automatic, and positioning errors may occur in this operation, solved by the present invention by the mechanical device and specially designed sensors so that the position is automatically corrected, thus avoiding reading errors;

3. Due to the wide variety of biological sample types, exam identification errors may occur, solved by the present patent through an automatic exam type identification system: the user doesn't need to inform which type of exam is required to be performed, because the code identifier (QR Code or similar) present in the cartridge allows the reader to identify what is the type of exam; and 4. Difficulty in registering new tests, making the operation difficult and time consuming. This problem has been solved by the present invention by automating the identification and positioning and setting of parameters that allow easy registration of new exams.

In order to obtain the technology of the present invention, incessant research and development was carried out through the following sequence:

Initially the company has always looked for solutions to facilitate and humanize health monitoring of sick people in a hospital setting. Although this approach reaches the people who need care the most, it represents a small portion of the people the company wants to reach. Due to this, some options were studied and considered to serve a larger part of the population as well as to facilitate health care.

Blood tests are widely performed by much of the population and provide important health information, thus enabling preventative measures to be taken to prevent serious events from being triggered. However, the process for taking the exams is bureaucratic.

[You first need to feel bad enough to go to the doctor, who will prescribe a battery of tests.

Then go to a laboratory to collect the biological material that will be submitted for analysis. Having the results in hand, the patient should return to the doctor, who will prescribe medication to treat the disease.

Since some methods used in laboratories can be used by the public, the idea has emerged of creating a product that can make testing as simple as measuring pressure or weight in the comfort of home.

Point-of-Care Tests (POCT) are easy to perform and require no laboratory structure. Pregnancy, menopause, and fertility tests can be found at drugstores, but there are yet another multitude of tests such as vitamin D, Sexually Transmitted diseases (STDs), drugs, and viruses.

The invention seeks to take advantage of commercially available tests and to facilitate their use. For this, the present product offers several types of cartridge-encapsulated quick exams and a reader for the interpretation of the exam result through the colorimetric principle. These features allow an untrained lay person to perform the exam of his or her choice with the same confidence as the one performed in the laboratory.

Figure 2:
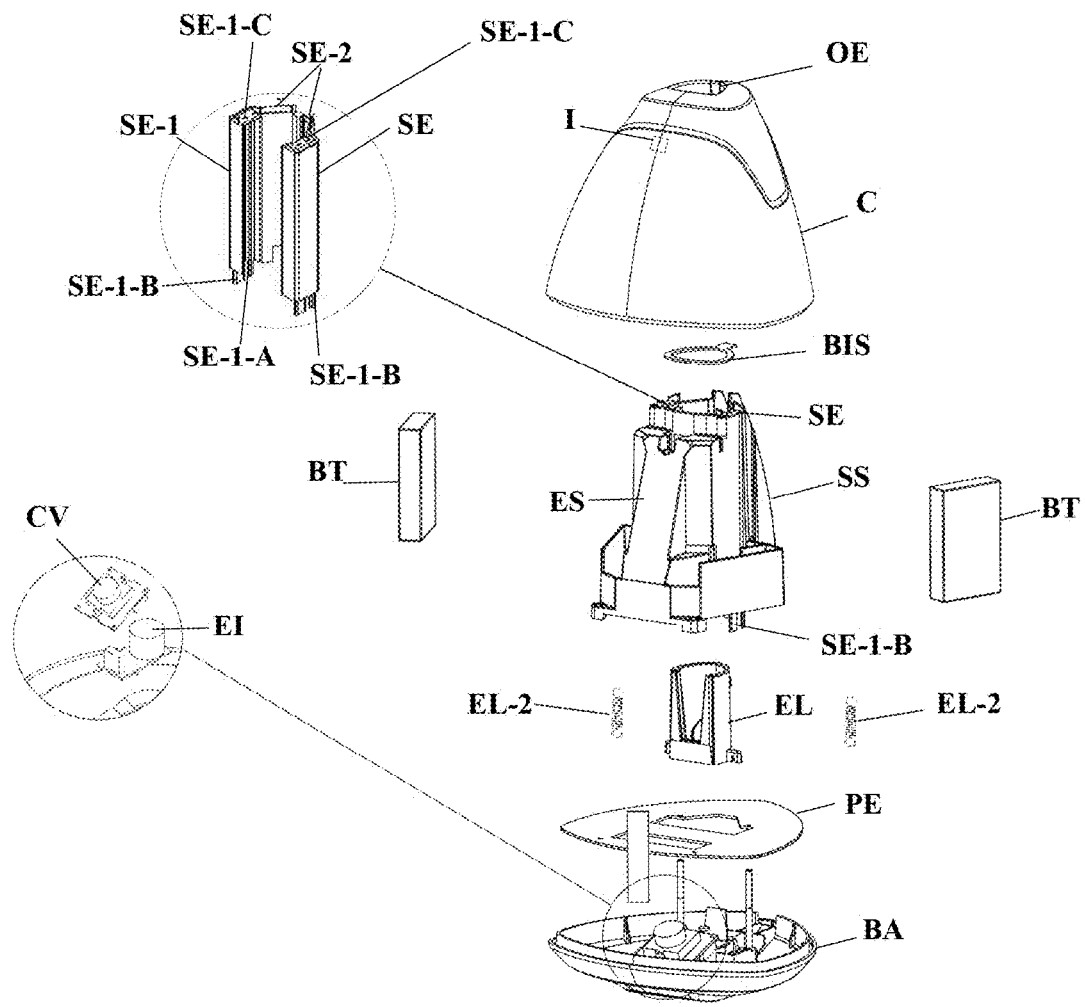
Figure 3:
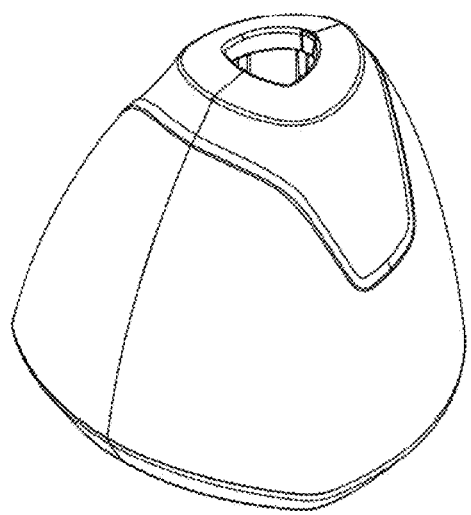
Figure 4:
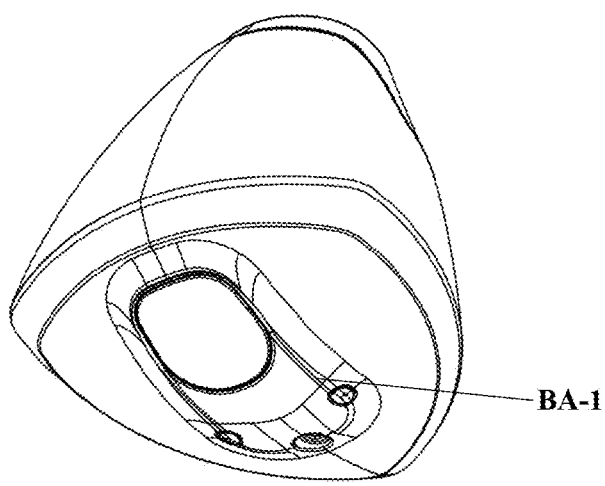
Figure 5:
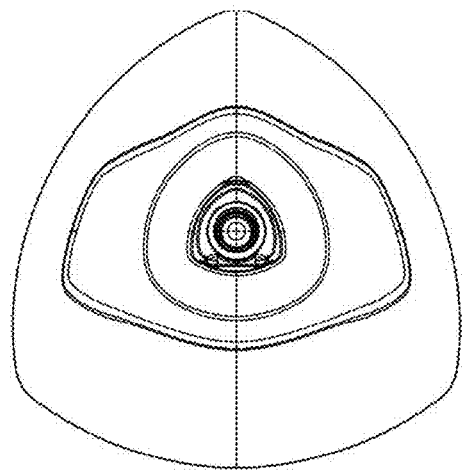
Figure 6:
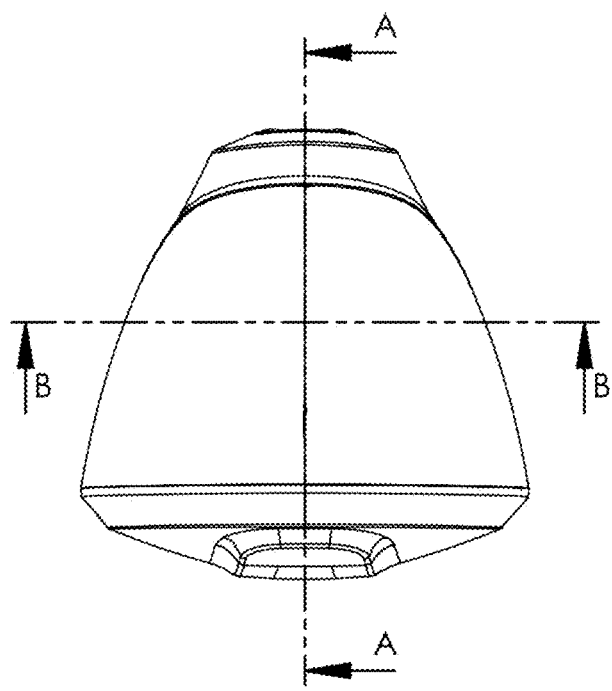
Figure 7:
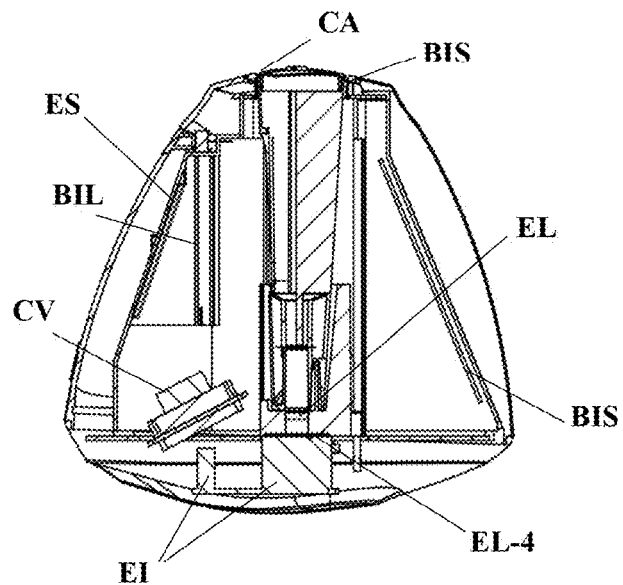
Figure 8:
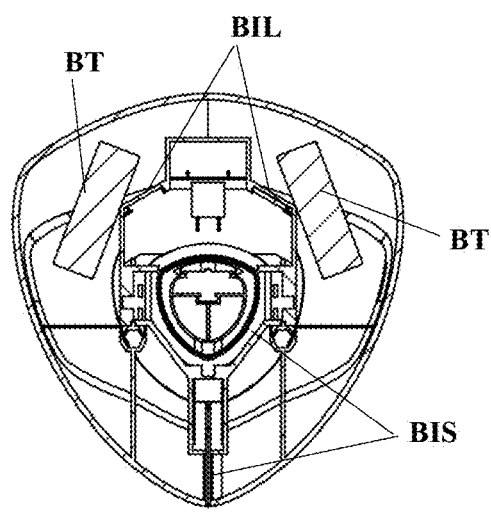
Figure 9:
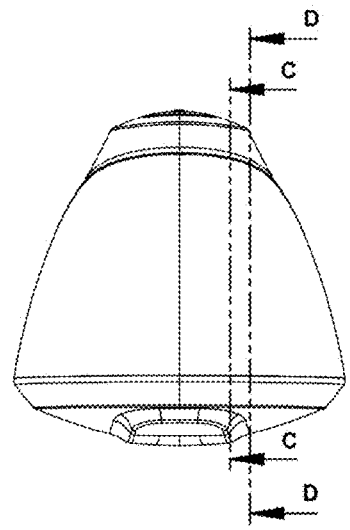
Figure 10:
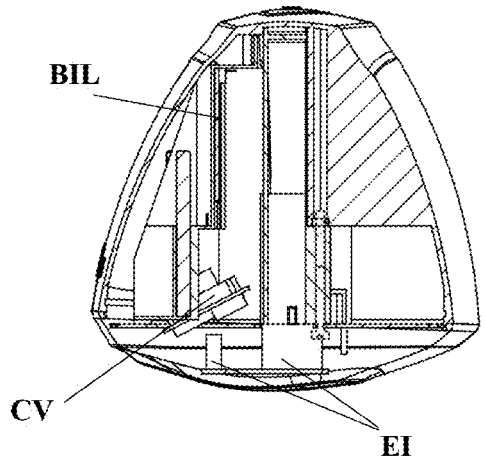
Figure 11:
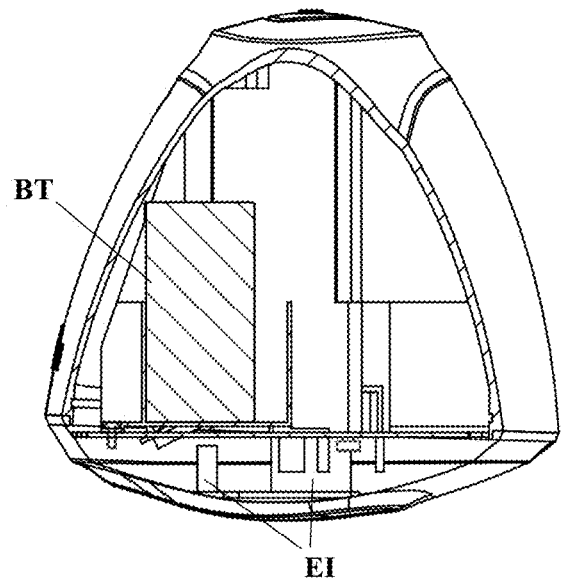
Figure 12:
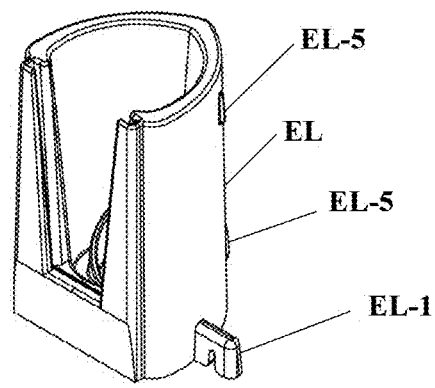
Figure 13:
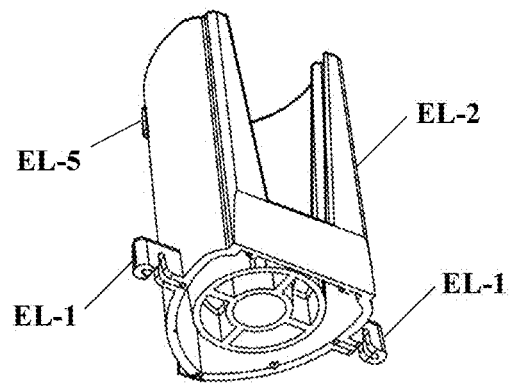
Figure 14:
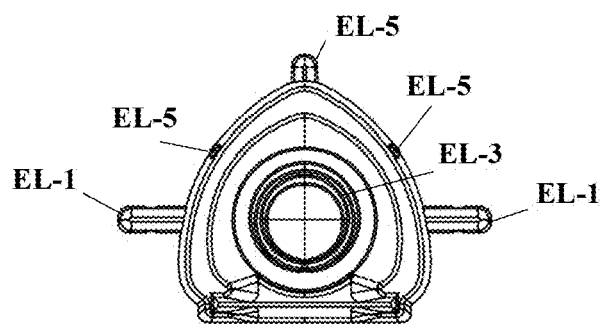
Figure 15:
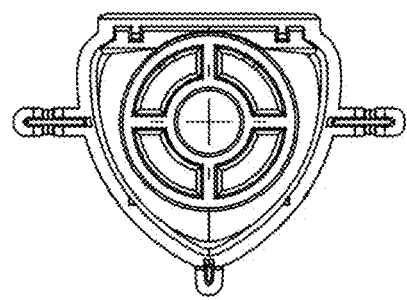
Figure 16:
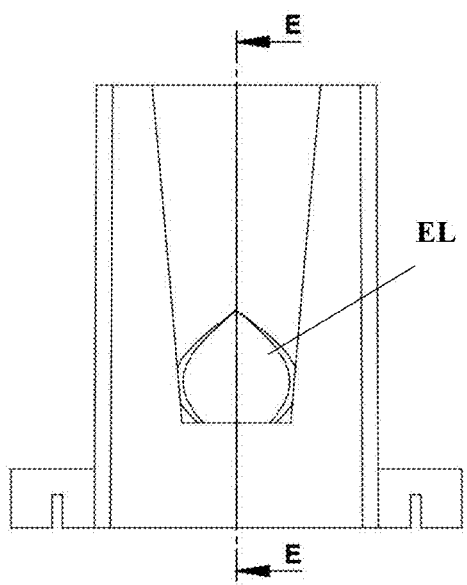
Figure 17:
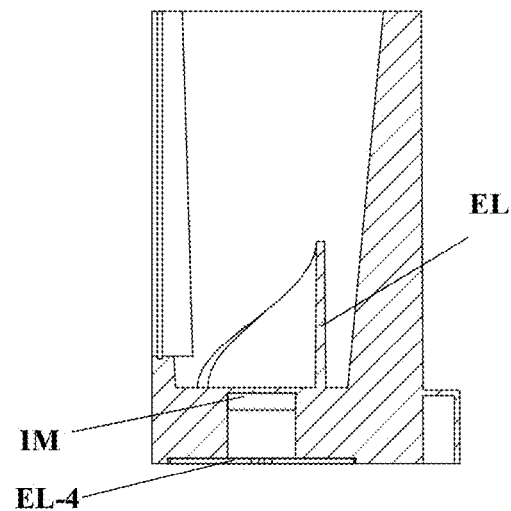
Figure 18:
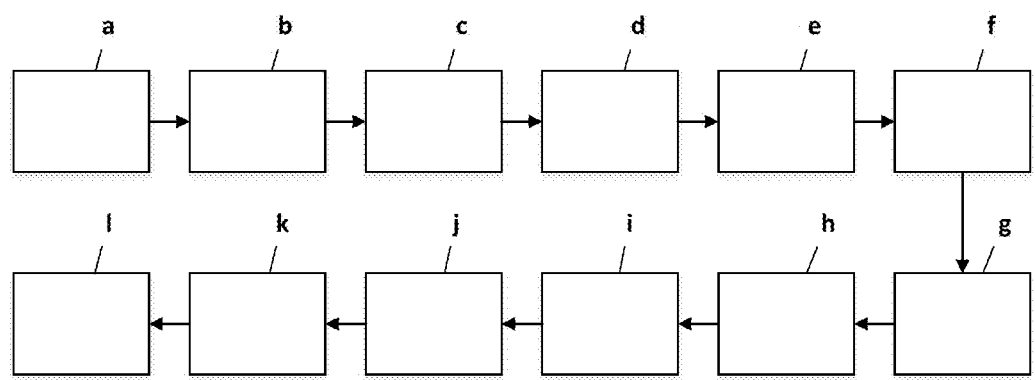

For a better understanding of this patent the following figures are attached:

FIG. 1, showing the block diagram of the components of test reader from the present patent;

FIG. 2, showing the exploded front perspective view of the test components of test reader from the present patent;

FIG. 3, showing the front perspective view of the assembled test reader from the present patent with no cartridge inserted;

FIG. 4, showing the bottom perspective of the test reader from the present patent;

FIG. 5, showing the top view of the test reader from the present patent;

FIG. 6, showing the front view with section indications AA and BB of the test reader from the present patent;

FIG. 7, showing the sectional view AA of the test reader from the present patent, with an inserted cartridge;

FIG. 8, showing the sectional view BB of the test reader from the present patent;

FIG. 9, showing the front view with indications of the CC and DD sections of the test reader from the present patent;

FIG. 10, showing the sectional view CC of the present invention;

FIG. 11, showing the sectional view DD of the test reader from the present patent;

FIG. 12, showing the side perspective view of the elevator of the test reader from the present patent;

FIG. 13, showing the bottom perspective view of the elevator of the test reader from the present patent;

FIG. 14, showing the top view of the elevator of the test reader from the present patent;

FIG. 15, showing the bottom view of the elevator of the test reader from the present patent;

FIG. 16, showing the front view of the elevator of the test reader from the present patent;

FIG. 17, showing the sectional view of the elevator of the test reader from the present patent; and FIG. 18, showing the block diagram of the complete process executed aided by dedicated software installed on the processor of the test reader from the present invention.

According to FIGS. 1 and 17, the reader of the present patent is constituted of fairing (C), in a conical frustum shape with an inlet orifice (OE) in a curved triangular shape, positioned on the upper side, with a capacitive-type switch (I) positioned on the upper inner side of the fairing flank; support holder (SS) in a pyramidal frustum shape, containing flat-shaped mirror (ES) on the outside and facing the elevator holder (SE) and the camcorder (CV), two lithium-batteries (BT) or any other similar batteries, in a rectangular prism shape at the outside, connected in series and unidirectionally connected to the power charging circuit (PE-1) and bidirectionally to the supply circuit (PE-2), two lighting bars for reading (BIL) with rectangular shaped LEDs, unidirectionally connected to the processor (PE-3) and to the supply circuit (PE-2) and positioned inside, lighting bars for indicating operational status (BIS) with one circular LED top and one rectangular LED inside and unidirectionally connected to processor (PE-3) and to the power circuit (PE-2) and C-shaped elevator support (SE) with two prismatic rectangular channels (SE-1) with U-shaped guide channels (SE-1-A) and pins (SE-1-B) at the bottom end engageable with the base (BA) and with bore holes (SE-1-C) for fitting of the springs (EL-2), and with two curved prismatic rectangular sides (SE-2); elevator (EL) in the shape of a hollow cylinder longitudinally cut with two prismatic rectangular shaped guide rails (EL-1) with curved rectangular cuts positioned on the lower outer flank and diametrically opposite to each other, two coil springs (EL-2) connected to the guides (EL-1) and to the holes (SE-1-C), with beveled hollow cylindrical shaped shoulder (EL-3) positioned at the bottom center of the elevator and with cylindrical shaped magnet (IM) positioned at the inner center of the shoulder (EL-3) and cartridge tip lock inside the elevator with rectangular prismatic metallic sheet (EL-4) positioned on the underside and rectangular prismatic shaped guides (EL-5) with rounded edges; electronic board (PE) with power charging circuit (PE-1) model BQ24105 or similar, unidirectionally connected to battery (BT) and external power supply (FA); with power supply (PE-2) model TPS62133 or similar connected unidirectionally to the processor (PE-3), to the Bluetooth® communication device (PE-4), to the position sensor (PE-5), to the reading lighting bars (BIL), to the operating status lighting bars (BIS), to the electromagnet (EI), and to the camcorder (CV), and bi-directionally to the battery (BT); with processor (PE-3) model Intel Edson or similar with memory (PE-3-A) recorded with dedicated software (SD) and unidirectionally connected to the power circuit (PE-2), to the Bluetooth® communication device (PE-4), to the position sensor (PE-5), to the operating status lighting bars (BIS), to the reading lighting bars (BIL), to the camcorder (CV) and the electromagnet (EI); with Bluetooth® communication device (PE-4) unidirectionally connected to the power circuit (PE-2) and to the processor (PE-3); and with infrared position sensor (PE-5) unidirectionally connected to the power circuit (PE-2) and to the processor (PE-3) and to the elevator position monitor (EL); and of torispherical cap-shaped base (BA) with rubber or similar non-slip adhesive (BA-1) on the bottom, with camcorder (CV) unidirectionally connected to the power circuit (PE-2) and to processor (PE-3) and for reading the sample contained in the cartridge (CA) and with electromagnet (EI) unidirectionally connected to the power circuit (PE-2) and processor (PE-3).

The process performed with the aid of dedicated software (SD) in the reader of the present invention is as follows, shown in FIG. 18:

a) The cartridge (CA) is manually inserted into the inlet orifice (OE) and the cartridge is inserted into the elevator (EL), stretching the springs (EL-2), passing through the shoulder (EL-3) until the metallic plate at the bottom of the cartridge (CA) touches the magnet (IM), causing the position correction by the cartridge (CA) guide and fixation in the elevator (EL);

b) The position sensor (PE-5) detects the presence of the elevator (E) with the cartridge (CA) and activates the electromagnet (EI) which magnetically attracts the metallic sheet (EL-4) holding the cartridge (CA) inside the reader;

c) reads the exam data contained in the cartridge (CA);

d) sends the cartridge (CA) code to the local remote hardware;

e) extracts parameters contained in the cartridge (CA) for performing exam;

f) are the parameters valid? If yes go to g), otherwise go to k);

g) waits time for reading;

h) captures images of the chemical reactions of the cartridge (CA) through the camcorder (CV);

i) interprets cartridge (CA) results;

j) send results to local remote hardware;

k) the electromagnet (EI) releases the cartridge (CA) through the springs (EL-2) that expels the cartridge (CA); and l) end.

The operation of the reader of the present invention is as follows:

a. Turn on the cartridge reader, when initialization is complete, the reader will turn green and if the battery is discharged it is necessary to connect to the mains through power supply (FA);

b. Turn on local remote hardware;

c. Connect with the cartridge reader;

d. Collect the user sample;

e. Place the sample in the region indicated on the cartridge;

f. Cap the cartridge;

g. Insert the cartridge into the slot indicated on the reader;

h. The cartridge (CA) will be identified and the exam information (name, collection type, duration) will appear on the local remote device;

i. If successfully recognized, the reader will flash and the cartridge should be inserted all the way and the scan will begin;

j. Reached the exam waiting time, the result will be displayed on local remote device;

k. Upon completion of the exam, result can be saved or discarded; and l. The cartridge (CA) is automatically released from the Reader.

What is claimed is:

1. A biological sample reader for biochemical testing, comprising:
　　a mirror;
　　a camcorder;
　　an electronic board;
　　an external power supply;
　　a power supply circuit;
　　a processor comprising a memory storage with dedicated software recorded on the memory storage;
　　a communication device;
　　a position sensor;
　　a fairing, arranged in a conical frustum shape comprising an inlet orifice arranged in a curved triangular shape, the inlet orifice positioned on an upper side of the fairing;
　　a capacitive switch positioned on an inner side of the fairing;
　　a support holder arranged in a pyramidal frustum shape, wherein the mirror is attached to the support holder and faces in a direction toward the camcorder disposed inside the fairing;
　　a battery attached to the support holder and disposed inside the fairing, the battery unidirectionally connected to a power charging circuit and bidirectionally connected to the power supply circuit;
　　a reading lighting bar comprising a plurality of rectangular shaped light emitting diodes (LEDs), the reading lighting bar unidirectionally connected to the processor and to the power supply circuit and positioned inside the fairing;
　　operational status lighting bars comprising a circular LED positioned adjacent a top of the fairing and a rectangular LED positioned inside the fairing, wherein the operational status lighting bars are unidirectionally connected to the processor and to the power supply circuit;
　　a C-shaped elevator support comprising two prismatic rectangular channels comprising U-shaped guide channels disposed therein and pins disposed at a bottom end of the C-shaped elevator support, the pins engageable with a base of the biological sample reader, wherein each prismatic rectangular channel of the two prismatic rectangular channels comprises holes, and wherein the C-shaped elevator support comprises two curved prismatic rectangular sides;
　　an elevator comprising a body in a hollow cylinder shape, the body comprising a longitudinal cut and two prismatic rectangular shaped guide rails protruding from an outer surface of the body, the two prismatic rectangular shaped guide rails each comprising a curved rectangular cut, wherein the two prismatic rectangular shaped guide rails are positioned on a lower portion of the body and are diametrically opposed to each other, and wherein the elevator comprises a rectangular prismatic shaped guide with rounded edges protruding from the outer surface of the body;
　　two coil springs connected to the two prismatic rectangular shaped guide rails and to the holes;
　　a beveled hollow cylindrical shaped shoulder positioned at a bottom center of the elevator;
　　an electromagnet positioned at an inner center of the beveled hollow cylindrical shaped shoulder; and
　　a cartridge tip lock disposed inside a portion of the elevator comprising a rectangular prismatic metallic plate positioned on an underside of the elevator;
　　wherein the electronic board comprises the power charging circuit, wherein the power charging circuit is unidirectionally connected to the external power supply, wherein the power supply circuit is unidirectionally connected to the communication device, the position sensor, the reading lighting bar, the operational status lighting bars, the electromagnet, and the camcorder, wherein the processor is unidirectionally connected to the power supply circuit, the communication device, the position sensor, the camcorder, and the electromagnet, wherein the position sensor is unidirectionally connected to an elevator position monitor of the elevator, and wherein the camcorder performs a reading of a sample contained in a cartridge that is positioned inside the elevator.

2. The biological sample reader for biochemical testing, according to claim 1, wherein the beveled hollow cylindrical shaped shoulder automatically corrects a position of the cartridge disposed inside the elevator maintaining the position of the cartridge inside the elevator when performing the reading of the sample contained in the cartridge.

3. The biological sample reader for biochemical testing, according to claim 1, wherein the battery provides power to the biological sample reader when external power is not provided to the biological sample reader via the external power supply and ensures that electrical failures do not interrupt performing the reading of the sample contained in the cartridge, and allows the biological sample reader to operate in places without externally provided electrical power.

4. The biological sample reader for biochemical testing according to claim 1, characterized by, the following sequence:
　　a) the cartridge is manually inserted into the inlet orifice of the fairing and into the elevator, wherein, as the cartridge is inserted into the elevator, the two coil springs stretch, and a portion of the cartridge passes through the beveled hollow cylindrical shaped shoulder until the rectangular prismatic metallic plate on the underside of the elevator touches the electromagnet, and maintains a position of the cartridge in the elevator;
　　b) the position sensor detects a presence of the elevator holding the cartridge and then activates the electromagnet that magnetically attracts the rectangular prismatic metallic plate magnetically holding the cartridge and the elevator in a testing position inside the biological sample reader;
　　c) the processor reads data associated with the cartridge;
　　d) the processor sends a cartridge code associated with the cartridge to a local remote hardware;
　　e) the processor determines whether parameters associated with the cartridge are valid for performing a biochemical test and, when the parameters are valid, the sequence proceeds to step
　　f), and, when the parameters are determined not to be valid, the sequence proceeds to step j)
　　f) wait an amount of time for reading;
　　g) capture images of chemical reactions of the sample contained in the cartridge through the camcorder;
　　h) interpret, from the images, results for the sample contained in the cartridge;
　　i) send the results to the local remote hardware;
　　j) the electromagnet releases the cartridge and the cartridge is ejected from the testing position; and
　　k) end.

* * * * *